United States Patent
Kuechler et al.

(10) Patent No.: US 9,115,060 B2
(45) Date of Patent: Aug. 25, 2015

(54) PROCESS FOR PRODUCING PHENOL

(75) Inventors: Keith H. Kuechler, Friendswood, TX (US); James R. Lattner, LaPorte, TX (US); Christopher L. Becker, Manhattan, KS (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/347,279

(22) PCT Filed: Aug. 29, 2012

(86) PCT No.: PCT/US2012/052876
§ 371 (c)(1),
(2), (4) Date: Jul. 14, 2014

(87) PCT Pub. No.: WO2013/052216
PCT Pub. Date: Apr. 11, 2013

(65) Prior Publication Data
US 2014/0330044 A1 Nov. 6, 2014

Related U.S. Application Data

(60) Provisional application No. 61/544,337, filed on Oct. 7, 2011.

(51) Int. Cl.
| | |
|---|---|
| C07C 45/53 | (2006.01) |
| C07C 37/08 | (2006.01) |
| C07C 37/07 | (2006.01) |
| C07C 2/74 | (2006.01) |
| C07C 407/00 | (2006.01) |
| C07C 49/403 | (2006.01) |

(52) U.S. Cl.
CPC . *C07C 37/07* (2013.01); *C07C 2/74* (2013.01); *C07C 37/08* (2013.01); *C07C 45/53* (2013.01); *C07C 49/403* (2013.01); *C07C 407/00* (2013.01); *C07C 2101/14* (2013.01); *C07C 2529/70* (2013.01)

(58) Field of Classification Search
CPC ........ C07C 45/53; C07C 37/08; C07C 29/143
USPC .......................................... 568/354, 799, 835
See application file for complete search history.

(56) References Cited

U.S. PATENT DOCUMENTS

| | | | |
|---|---|---|---|
| 2,265,939 | A | 12/1941 | Field |
| 3,256,348 | A | 6/1966 | Schlossman |
| 4,021,490 | A | 5/1977 | Hudson |
| 4,230,638 | A | 10/1980 | Murtha |
| 5,180,871 | A | 1/1993 | Matsunaga et al. |
| 2011/0021844 | A1 | 1/2011 | Dakka et al. |
| 2011/0105805 | A1* | 5/2011 | Buchanan et al. ............ 568/798 |

FOREIGN PATENT DOCUMENTS

| | | | |
|---|---|---|---|
| GB | | 680509 | 10/1952 |
| GB | | 929680 | 6/1963 |
| GB | | 939613 | 10/1963 |
| GB | | 1194686 | 6/1970 |
| WO | WO 2009/025939 | | 2/2009 |
| WO | WO 2009/058527 | | 5/2009 |
| WO | WO 2009/058531 | | 5/2009 |
| WO | WO 2009/128984 | | 10/2009 |
| WO | WO 2009/131769 | | 10/2009 |
| WO | WO 2010/024975 | | 3/2010 |
| WO | WO2010098916 | * | 9/2010 |
| WO | WO 2012/036818 | | 3/2012 |
| WO | WO 2012/036826 | | 3/2012 |
| WO | WO 2012/036827 | | 3/2012 |
| WO | WO 2012/036828 | | 3/2012 |
| WO | WO 2012/082407 | | 6/2012 |

* cited by examiner

*Primary Examiner* — Sikarl Witherspoon
(74) *Attorney, Agent, or Firm* — Siwen Chen; Stephen A. Baehl

(57) ABSTRACT

In a process for producing phenol, cyclohexylbenzene hydroperoxide is cleaved to produce a cleavage effluent stream comprising phenol and cyclohexanone and at least a portion of the cleavage effluent stream is fractionated to produce a first fraction richer in cyclohexanone than the cleavage effluent stream portion and a second fraction richer in phenol and depleted in cyclohexanone as compared with said cleavage effluent stream portion. At least a portion of the second fraction is then contacted with a dehydrogenation catalyst in a dehydrogenation reaction zone under dehydrogenation conditions effective to convert at least a portion of the cyclohexanone in said second fraction portion into phenol and cyclohexanol.

14 Claims, 3 Drawing Sheets

PROCESS FOR PRODUCING PHENOL

PRIORITY CLAIM

This application is a National Stage Application of International Application No. PCT/US2012/052876 filed Aug. 29, 2012, which claims priority to U.S. Provisional Application Ser. No. 61/544,337 filed Oct. 7, 2011, the disclosures of which are fully incorporated herein by their reference.

FIELD

The present invention relates to a process for producing phenol.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, the cost of propylene is likely to increase, due to a developing shortage of propylene. Thus, a process that uses higher alkenes instead of propylene as feed and coproduces higher ketones, rather than acetone, may be an attractive alternative route to the production of phenols.

For example, oxidation of the cyclohexylbenzene (analogous to cumene oxidation) could offer an alternative route for phenol production without the problem of acetone co-production. This alternative route proceeds through cyclohexylbenzene hydroperoxide, which is cleaved to produce phenol and cyclohexanone in substantially equimolar amounts.

However, one problem in producing phenol by way of the cleavage of cyclohexylbenzene hydroperoxide is that the cyclohexanone and phenol produce an azeotropic mixture composed of 28 wt % cyclohexanone and 72 wt % phenol. Thus, one cannot recover all of the cyclohexanone, or any of the phenol, from the cleavage effluent as a saleable product by simple distillation. Moreover, although cyclohexanone is a valuable product with a growing market, there is currently no large worldwide merchant market for cyclohexanone; most cyclohexanone is made as an intermediate and consumed on the spot. In some cases, therefore, it may be desirable to increase the amount of phenol in the product mix from the cleavage of cyclohexylbenzene hydroperoxide or even produce all phenol with no cyclohexanone.

For example, U.S. Published Patent Application No. 2011/0105805 discloses a process for producing phenol by oxidation of cyclohexylbenzene to cyclohexylbenzene hydroperoxide followed by cleavage of the cyclohexylbenzene hydroperoxide, in which some or all of the effluent from the cleavage step is subjected to a selective dehydrogenation step to convert at least a portion of the cyclohexanone in the effluent portion into phenol and hydrogen. Where only part of the cleavage effluent is dehydrogenated, the effluent is initially subjected to at least a first separation step to recover some or all of the phenol from the effluent, typically so that the effluent stream fed to said dehydrogenation reaction contains less than 50 wt %, for example less than 30 wt %, such as less than 1 wt %, phenol. Additional distillation steps can be used to remove components boiling below 155° C. (as measured at 101 kPa), such as benzene and cyclohexene, and/or components boiling above 185° C. (as measured at 101 kPa), such as 2-phenyl phenol and diphenyl ether, prior to feeding the effluent stream to the dehydrogenation reaction.

One problem with the process proposed in U.S. Published Patent Application No. 2011/0105805 is that expensive vacuum and/or extractive distillation methods are required to recover the phenol before the remainder of the effluent is fed to the dehydrogenation reaction. To address this problem, the present invention proposes alternative approach to increasing the amount of phenol in the product mix from the cleavage of cyclohexylbenzene hydroperoxide. Thus, in accordance with the invention, cyclohexanone is separated from the cleavage effluent, typically by conventional distillation and preferably to reduce the cyclohexanone content of the effluent to approach the azeotropic amount of 28 wt %. According to market conditions, the cyclohexanone can then be recovered as a usable product or dehydrogenated to produce phenol, whereas the remainder of the cleavage effluent, potentially an azeotropic mixture of phenol and cyclohexanone, is subjected to selective dehydrogenation to convert the cyclohexanone to phenol.

Cyclohexanone is typically produced by the oxidation of cyclohexane, or the hydrogenation of phenol. These methods can also generate various contaminants that are difficult to separate from the desired product, and that can render the cyclohexanone product substandard or unusable to downstream processes, for example in the manufacture of caprolactam or adipic acid, or further using those derivatives in the production of one or another type of nylon. Such contaminants include butylcyclohexylether, pentylcyclohexane, cyclohexyl acetate, pentanal, valeric acid and butyric acid.

The production of cyclohexanone from cyclohexylbenzene (with phenol as a co-product) is an emerging technology. The production of cyclohexanone from cyclohexylbenzene also produces various contaminants that are difficult to separate from the desired products. However, the nature of those contaminants and the separations involved are significantly different than those involved in the conventional production of cyclohexanone from cyclohexane or phenol. For example, hydroalkylation of benzene produces significant amounts of, inter alia, cyclohexane and lesser amounts of methylcyclopentane, cyclohexene, phenylcyclohexene, and phenylcyclohexyldiene. Similarly, the oxidation of cyclohexylbenzene typically produces peroxide species alien to conventional processes for making cyclohexanone, such as the desired cyclohexyl-1-phenyl-1-hydroperoxide (CHBHP), and undesired byproduct hydroperoxides such as cyclohexyl-1-phenyl-2-hydroperoxide, cyclohexyl-1-phenyl-3-hydroperoxide and cyclohexyl-1-phenyl-4-hydroperoxide. Finally, the cleavage of these various hydroperoxides produces, as both the product of the undesired hydroperoxides and the undesired byproducts of the desired CHBHP, a wide variety of contaminant species are not produced by the chemistry and technology of the cyclohexane oxidation or phenol hydrogenation processes, such as cyclohexanedione and hydroxycyclohexanone.

SUMMARY

In one aspect, the invention resides in a process for producing phenol, the process comprising:
(a) cleaving cyclohexylbenzene hydroperoxide to produce a cleavage effluent stream comprising phenol and cyclohexanone;

(b) fractionating at least a portion of the cleavage effluent stream to produce a first fraction richer in cyclohexanone than said portion of the cleavage effluent stream and a second fraction richer in phenol and depleted in cyclohexanone as compared with said portion of the cleavage effluent stream; and (c) contacting at least a portion of the second fraction with a dehydrogenation catalyst in a dehydrogenation reaction zone under dehydrogenation conditions effective to convert at least a portion of the cyclohexanone in said portion of the second fraction into phenol and cyclohexanol.

Conveniently, the first fraction comprises no more than 1000 ppm of phenol, based upon the total weight of the first fraction.

Conveniently, the weight ratio of phenol to cyclohexanone in said portion of the cleavage effluent stream is less than or equal to 2.57, such as about 0.7 to about 1.5, and the fractionating (b) is effected by simple distillation.

Conveniently, the weight ratio of phenol to cyclohexanone in said second fraction is about 2.0 to about 2.5.

Conveniently, the contacting (c) produces (i) a product stream comprising phenol, cyclohexanol and cyclohexanone; and (ii) a hydrogen stream.

Conveniently, the process further comprises:
(d) recovering a phenol-containing stream from said product stream to leave a residual stream comprising cyclohexanol and cyclohexanone; and (e) contacting at least a portion of the residual stream with a dehydrogenation catalyst in a dehydrogenation reaction zone under dehydrogenation conditions effective to convert at least a portion of the cyclohexanol and cyclohexanone in said portion of the residual stream into phenol and produce (i) a product stream comprising phenol, cyclohexanol and cyclohexanone; and (ii) a hydrogen stream.

In one embodiment, the phenol-containing stream recovered in (d) contains less than 1 wt % of cyclohexanone and cyclohexanol combined. Generally, the weight ratio of phenol to cyclohexanone in said product stream is greater than 2.57 and said phenol-containing stream is recovered from said product stream in (d) by simple distillation.

Conveniently, said portion of the residual stream and said portion of the second fraction are contacted with a dehydrogenation catalyst in the same dehydrogenation reaction zone.

Conveniently, the process further comprises:
(f) recycling at least a portion of said further product stream to said recovering (d); and (g) repeating said recovering (d), said contacting (e) and said recycling (f) to convert at least 90 wt % of the cyclohexanone in the second fraction to phenol.

In a further aspect, the invention resides in a process for producing phenol from benzene, the process comprising:
(a) contacting benzene and hydrogen with a catalyst under hydroalkylation conditions to produce cyclohexylbenzene;

(b) oxidizing at least a portion of the cyclohexylbenzene from (a) to produce an oxidation effluent stream comprising cyclohexylbenzene hydroperoxide and cyclohexylbenzene;

(c) cleaving cyclohexylbenzene hydroperoxide in at least a portion of said oxidation effluent stream to produce a cleavage effluent steam comprising phenol, cyclohexanone and cyclohexylbenzene;

(d) fractionating at least a portion of the cleavage effluent stream to produce a first fraction richer in cyclohexanone than said portion of the cleavage effluent stream and a second fraction richer in phenol and depleted in cyclohexanone as compared with said portion of the cleavage effluent stream; and (e) contacting at least a portion of the second fraction with a dehydrogenation catalyst in a dehydrogenation reaction zone under dehydrogenation conditions effective to convert at least a portion of the cyclohexanone in said portion of the second fraction into phenol and cyclohexanol and produce a product stream comprising phenol, cyclohexanol and cyclohexanone and a hydrogen stream.

Conveniently, the process further comprises:
(f) removing a third fraction comprising cyclohexylbenzene from at least a portion of the cleavage effluent stream so that said second fraction contains less than 2 wt % cyclohexylbenzene.

In yet a further aspect, the invention resides in a composition comprising: (a) at least 99 wt % cyclohexanone; (b) 0.1 wppm to 400 wppm of cyclohexanol and (c) 0.1 wppm to 100 wppm of at least one of methylcyclopentenone, cyclohexenol, cyclohexanedione and hydroxycyclohexanone, wherein the wt % and wppm are based upon the total weight of the composition. Conveniently, the composition comprises less than 1 wppm of one or more of methylcyclopentenone, methylcyclopentenal, cyclohexenone, cyclohexenol, phenol, butylcyclohexylether, pentylcyclohexane, cyclohexyl acetate, pentanal, valeric acid, and butyric acid. In another embodiment, the composition comprises 0.1 wppm to 1000 wppm of water as determined according to DIN 51777/Part 1, based upon the total weight of the composition.

DETAILED DESCRIPTION OF THE EMBODIMENTS

Figure 1:
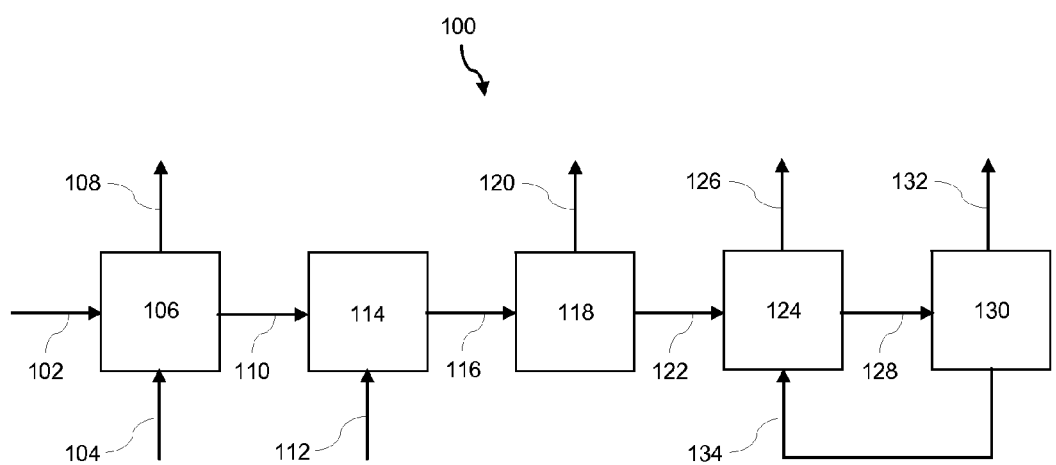
FIG. 1 is a schematic view of a simplified process for producing phenol and cyclohexanone from cyclohexylbenzene in accordance with a first example of the present invention.

Described herein is a process for producing phenol and cyclohexanone by cleavage of cyclohexylbenzene hydroperoxide. In the present process, the production of phenol is enhanced by separating cyclohexanone from the cleavage effluent, typically by conventional distillation, to leave an effluent fraction with reduced cyclohexanone content typically approaching the azeotropic amount of 28 wt %. This effluent fraction is then subjected to dehydrogenation to convert at least a portion of the cyclohexanone into phenol and cyclohexanol and produce a product stream comprising phenol, cyclohexanol and cyclohexanone and a hydrogen stream. Phenol is recovered from this product stream to leave a residual stream which comprises cyclohexanol and cyclohexanone and which can be recycled to the dehydrogenation process. By repeating the phenol recovery and dehydrogenation processes, it is possible to convert at least 90 wt % of the cyclohexanone produced in the effluent fraction to phenol.

The cyclohexanone product of the present process, after separation from the cleavage effluent, is of exceptional quality for further processing, in say, caprolactam production, relative to both the conventional cyclohexane oxidation and phenol hydrogenation processes, containing far fewer impurities, with those impurities having a significantly lower impact on the downstream process steps and the product.

In one preferred embodiment, the present process forms part of an integrated process for producing cyclohexanone and phenol from benzene in which the benzene is initially converted to cyclohexylbenzene, conveniently by hydroalkylation. The cyclohexylbenzene is then oxidized to produce cyclohexylbenzene hydroperoxide, which is then subjected to the cleavage, separation and dehydrogenation operations discussed above. The ensuing description will therefore focus on this integrated process.

Production of the Cyclohexylbenzene

One step of the integrated process starting from benzene, cyclohexylbenzene is produced by reacting the benzene with cyclohexene in the presence of a catalyst having an alkylation function and under conditions to promote the following reaction:

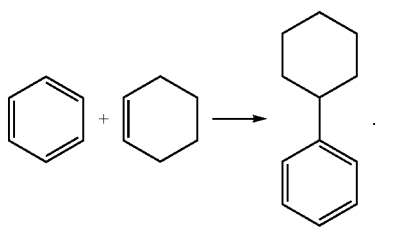

The cyclohexene can be supplied to the reaction zone as a separate feed from the benzene, but normally is produced in situ by selective hydrogenation of the benzene in the presence of a hydrogenation component provided on the catalyst having the alkylation function. The bifunctional catalyst is therefore referred to herein as a hydroalkylation catalyst and overall the hydroalkylation reaction proceeds as follows to produce cyclohexylbenzene (CHB):

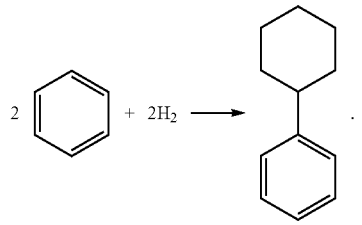 [SMILES: c1ccccc1 ; c1ccc(C2CCCCC2)cc1]

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

In one embodiment, the total feed to the hydroalkylation step contains less than 1000 ppm, such as less than 500 ppm, for example less than 100 ppm, water. In various embodiments, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Typically the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Å Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25

(described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with said molecular sieve. Typically, the catalyst composite is produced by co-pelletization, in which a mixture of the molecular sieve and the metal-containing inorganic oxide are formed into pellets at high pressure (generally about 350 to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation reaction using an MCM-22 family zeolite catalyst activated by the process described herein is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y and mordenite. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 $hr^{-1}$ on total feed, and a benzene/dicyclohexylbenzene weight ratio about of 1:1 to about 5:1.

Dealkylation or cracking is also typically effected in a reactor separate from the hydroalkylation reactor, such as a reactive distillation unit, at a temperature of about 150° C. to about 500° C. and a pressure of 15 to 500 psig (200 to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia and mixtures thereof Generally, the acid catalyst includes at least one aluminosilicate, aluminophosphate or silicoaluminphosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically is from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least a portion of the cyclohexane in the $C_6$-rich stream portion to benzene, which again can be recycled to the hydroalkylation reaction. The dehydrogenation catalyst generally comprises (a) a support; (b) a hydrogenation-dehydrogenation component and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. Typically, the hydrogenation-dehydrogenation component is present in an amount between about 0.1 and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 and about 5 wt % of the catalyst. Suitable dehydrogenation conditions include a temperature of about 250° C. to about 500° C., a pressure of about atmospheric to about 500 psig (100 to 3550 kPa), a weight hourly space velocity of about 0.2 to 50 $hr^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least a portion of the hydroalkylation reaction product may be treated with a catalyst under conditions to remove at least 1,1-methylcyclopentylbenzene and/or bicyclohexyl from the product. The catalyst is generally an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

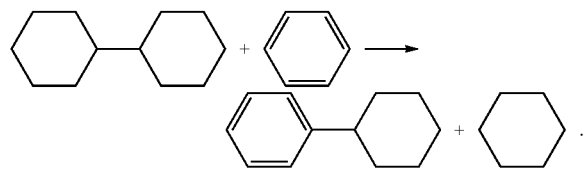

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed above is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene may be oxidized to the corresponding hydroperoxide. This is accomplished by contacting the cyclohexylbenzene with an oxygen-containing compound, such as air and various derivatives of air. For example, it is possible to use air that has been compressed and filtered to remove particulates, air that has been compressed and cooled to condense and remove water, or air that has been enriched in oxygen above the natural approximately 21 mol % in air through membrane enrichment of air, cryogenic separation of air, or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. Preferably, the catalyst is N-hydroxyphthalimide. Another suitable catalyst is N,N',N"-thihydroxyisocyanuric acid.

These oxidation catalysts can be used either alone or in conjunction with a free radical initiator, and further can be used as liquid-phase, homogeneous catalysts, or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 wt % to 5 wt %, of the cyclohexylbenzene. The use of such oxidation catalysts in the manner disclosed herein conveniently facilitates a high selectivity to the desired cyclohexyl-1-phenyl-1-hydroperoxide, although other hydroperoxides may also be formed in varying quantities and be present in the oxidation effluent.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaceously provide contacting of oxygen and cyclohexylbenzene to effect the oxidation reaction. For example, the oxidation reactor may comprise a simple, largely open vessel with a distributor inlet for the oxygen-containing stream. In various embodiments, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation effluent. Generally, the oxidation effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation effluent. The oxidation effluent may further comprise imide catalyst and unreacted cyclohexylbenzene. For example, the oxidation effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation effluent.

At least a portion of the oxidation effluent may be subjected to a cleavage reaction, with or without undergoing any prior separation or treatment. For example, all or a fraction of the oxidation effluent may be subjected to high vacuum distillation to generate a product enriched in unreacted cyclohexylbenzene and leave a residue which is concentrated in the desired cyclohexyl-1-phenyl-1-hydroperoxide and which is subjected to the cleavage reaction. In general, however, such concentration of the cyclohexyl-1-phenyl-1-hydroperoxide is neither necessary nor preferred. Additionally or alternatively, all or a fraction of the oxidation effluent, or all or a fraction of the vacuum distillation residue may be cooled to cause crystallization of the unreacted imide oxidation catalyst, which can then be separated either by filtration or by scraping from a heat exchanger surface used to effect the crystallization. At least a portion of the resultant oxidation composition reduced or free from imide oxidation catalyst may be subjected to the cleavage reaction.

As another example, all or a fraction of the oxidation effluent may be subjected to water washing and then passage through an adsorbent, such as a 3A molecular sieve, to separate water and other adsorbable compounds, and provide an oxidation composition with reduced water or imide content that may be subjected to the cleavage reaction. Similarly, all or a fraction of the oxidation effluent may undergo a chemically or physically based adsorption, such as passage over a bed of sodium carbonate to remove the imide oxidation catalyst (e.g., NHPI) or other adsorbable components, and provide an oxidation composition reduced in oxidation catalyst or other adsorbable component content that may be subjected to the cleavage reaction. Another possible separation involves contacting all or a fraction of the oxidation effluent with a liquid containing a base, such as an aqueous solution of an alkali metal carbonate or hydrogen carbonate, to form an aqueous phase comprising a salt of the imide oxidation catalyst, and an organic phase reduced in imide oxidation catalyst. An example of separation by basic material treatment is disclosed in International Publication No. WO 2009/025939.

Hydroperoxide Cleavage

Another reactive step in the conversion of the cyclohexylbenzene into phenol and cyclohexanone involves the acid-catalyzed cleavage of the cyclohexyl-1-phenyl-1-hydroperoxide produced in the oxidation step. Other hydroperoxides that may be present in the oxidation effluent stream may also undergo acid-catalyzed cleavage along with the desired cyclohexyl-1-phenyl-1-hydroperoxide.

Generally, the acid catalyst used in the cleavage reaction is at least partially soluble in the cleavage effluent, is stable at a temperature of at least 185° C. and has a lower volatility (higher normal boiling point) than cyclohexylbenzene. Typically, the acid catalyst is also at least partially soluble in the cleavage reaction product. Suitable acid catalysts include, but are not limited to, Brønsted acids, Lewis acids, sulfonic acids, perchloric acid, phosphoric acid, hydrochloric acid, p-toluene sulfonic acid, aluminum chloride, oleum, sulfur trioxide, ferric chloride, boron trifluoride, sulfur dioxide, and sulfur trioxide. Sulfuric acid is a preferred acid catalyst.

In various embodiments, the cleavage effluent contains at least 50 weight-parts-per-million (wppm) and no greater than 5000 wppm of the acid catalyst, or at least 100 wppm and no greater than 3000 wppm, or at least 150 wppm and no greater than 2000 wppm of the acid catalyst, or at least 300 wppm and no greater than 1500 wppm of the acid catalyst, based upon total weight of the cleavage effluent.

In other embodiments, a heterogeneous acid catalyst is employed for the cleavage reaction, such as molecular sieve, and in particular a molecular sieve having a pore size in excess of 7 Å. Examples of suitable molecular sieves include zeolite beta, zeolite Y, zeolite X, ZSM-12, and mordenite. In one embodiment, the molecular sieve comprises a FAU type zeolite having a unit cell size less than 24.35 Å, such as less than or equal to 24.30 Å, even less than or equal to 24.25 Å. The zeolite can be used in unbound form or can be combined with a binder, such as silica or alumina, such that the overall catalyst (zeolite plus binder) comprises from about 20 wt % to about 80 wt % of the zeolite.

The cleavage effluent may contain a polar solvent, such as an alcohol containing less than 6 carbons, such as methanol, ethanol, iso-propanol, and/or ethylene glycol; a nitrile, such as acetonitrile and/or propionitrile; nitromethane; and a ketone containing 6 carbons or less, such as acetone, methylethyl ketone, 2- or 3-pentanone, cyclohexanone, and methylcyclopentanone. The preferred polar solvent is phenol and/or cyclohexanone recycled from the cleavage product after cooling. Generally, the polar solvent is added to the cleavage effluent such that the weight ratio of the polar solvent to the cyclohexylbenzene hydroperoxide in the mixture is in the range of about 1:100 to about 100:1, such as about 1:20 to about 10:1, and the mixture comprises about 10 wt % to about 40 wt % of the cyclohexylbenzene hydroperoxide. The addition of the polar solvent is found not only to increase the degree of conversion of the cyclohexylbenzene hydroperoxide in the cleavage reaction but also to increase the selectivity of the conversion to phenol and cyclohexanone. Although the mechanism is not fully understood, it is believed that the polar solvent reduces the free radical inducted conversion of the cyclohexylbenzene hydroperoxide to undesired products such as hexanophenone and phenylcyclohexanol.

In various embodiments, the cleavage effluent includes cyclohexylbenzene in an amount of at least 50 wt %, or at least 60 wt %, or at least 65 wt %, or at least 70 wt %, or at least 80 wt %, or at least 90 wt %, based upon total weight of the cleavage effluent.

Generally, the cleavage reaction is conducted under conditions including a temperature of about 20° C. to about 200° C., such as about 40° C. to about 120° C. and a pressure of about 100 kPa to about 2000 kPa, such as about 100 kPa to about 1000 kPa, such that the cleavage effluent is completely or predominantly in the liquid phase during the cleavage reaction.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. In other embodiments, the cleavage reactor comprises a plurality of reactors in series, each performing a portion of the conversion reaction, optionally operating in different modes and at different conditions selected to enhance the cleavage reaction at the pertinent conversion range. In one embodiment, the cleavage reactor is a catalytic distillation unit.

In various embodiments, the cleavage reactor is operable to transport a portion of the contents through a cooling device and return the cooled portion to the cleavage reactor, thereby managing the exothermicity of the cleavage reaction. Alternatively, the reactor may be operated adiabatically. In one embodiment, cooling coils operating within the cleavage reactor(s) remove any heat generated.

The major products of the cleavage reaction of cyclohexyl-1-phenyl-1-hydroperoxide are phenol and cyclohexanone in proportions such the weight ratio of phenol to cyclohexanone in the cleavage effluent (wt % phenol/wt % cyclohexanone) is less than or equal to 2.57, such as from about 0.7 to about 1.5, for example from about 0.8 to about 1.2. In other words, the cleavage effluent contains more cyclohexanone than the 28 wt % present in the azeotropic mixture of phenol and cyclohexanone. Thus, simple distillation can be used to remove cyclohexanone from the cleavage effluent and leave an effluent fraction with reduced cyclohexanone content typically approaching the azeotropic amount of 28 wt %.

In addition, to phenol and cyclohexanone, the cleavage effluent may contain from about 0.1 wt % to about 10 wt %, such as from about 0.5 wt % to about 7 wt %, for example from about 1 wt % to about 5 wt % of contaminant by-products (the wt % based upon the total weight of the cleavage effluent), particularly:

- non-oxygenated unsaturated hydrocarbons, cyclic and acyclic, or combinations thereof, such as cyclohexene, possibly in the range of 10 wppm to 1.0 wt %.
- unsaturated alkyl benzene(s), especially unsaturated cyclic alkyl benzene(s), such as phenyl cyclohexene, possibly in the range of 10 wppm to 4.0 wt %.
- cyclohexanol, possibly no greater than 1.0 wt %, or no greater than 1000, or 500, or 100, or 50, or 10 wppm.
- cyclohexenone, especially 2-cyclohexenone, possibly no greater than 1.0 wt %, or no greater than 1000, or 500, or 100, or 50, or 10 wppm.
- methcyclopentanone, possibly in the range of 10 wppm to 2.0 wt %.
- other saturated and unsaturated ketones, such as pentanones, hexanones, 1-phenylhexan-1-one, and 1-cyclohexylhexan-1-one, possibly in the range of 10 wppm to 2.0 wt %.
- hydroxycyclohexanone(s), especially 2-hydroxycyclohexanone, possibly in the range of 10 wppm to 2.0 wt %.
- carboxylic acids, especially benzoic acid, possibly in the range of 10 wppm to 1.0 wt %.
- phenyl cyclohexanol(s), such as 2-phenylcyclohexanol, possibly in the range of 10 wppm to 4.0 wt %.
- cyclohexyl cyclohexanol(s), such as 2-cyclohexylcyclohexanol, possibly in the range of 10 wppm to 1.0 wt %.
- unsaturated alkyl oxygenated cyclohexanes, especially cyclohexenyl cyclohexanols and cyclohexenyl cyclohexanones, and methylcyclopentenyl cyclohexanols and methylcyclopentenyl cyclohexanones, possibly in the range of 10 wppm to 1.0 wt %.
- cyclohexyldione(s), possibly in the range of 10 wppm to 1.0 wt %.
- aldehydes, especially, pentanals, hexanals, cyclohexyl, or methylcyclopentyl alkyl aldehydes, such as 5-cyclohexyl hexanal, and 6-hydoxy-5-cyclohexyl hexanal, possibly no greater than 1.0 wt %, or no greater than 1000, or 500, or 100, or 50, or 10 wppm individually, or possibly in the range of 10 wppm to 1.0 wt % totally.
- 1-phenyl-6-hydroxyhexan-1-one, possibly in the range of 10 wppm to 4.0 wt %.
- 1-cyclohexyl-6-hydroxyhexan-1-one, possibly in the range of 10 wppm to 1.0 wt %.
- benzoic esters, possibly in the range of 10 wppm to 1.0 wt %.
- Unreacted hydroperoxides. Non-limiting examples include: cyclohexyl-1-phenyl-1-hydroperoxide, cyclohexyl-1-phenyl-2-hydroperoxide, cyclohexyl-1-phenyl-3-hydroperoxide, cyclohexyl-1-phenyl-4-hydroperoxide; cyclopentyl-1-methyl-2-phenyl-2-hydroperoxide, cyclopentyl-1-methyl-3-phenyl-3-hydroperoxide, cyclopentyl-1-methyl-1-phenyl-2-hydroperoxide, cyclopentyl-1-methyl-1-phenyl-3-hydroperoxide; any isomer of phenylcyclohexanone hydroperoxide or phenylcyclohexanol hydroperoxide, such as cyclohexanone-2-phenyl-2-hydroperoxide or cyclohexanol-2-phenyl-2-hydroperoxide, the precursors of 1,2-cyclohexanedione and 2-hydroxycyclohexanone, respectively; and cyclohexyl-1-phenyl-1,2-dihydroperoxide, cyclohexyl-1-phenyl-1,3-dihydroperoxide, cyclohexyl-1-phenyl-1,4-dihydroperoxide; cyclopentyl-1-methyl-2-phenyl-1,2-dihydroperoxide, cyclopentyl-1-methyl-2-phenyl-2,3-dihydroperoxide, cyclopentyl-1-methyl-2-phenyl-2,4-dihydroperoxide, cyclopentyl-1-methyl-2-phenyl-2,5-dihydroperoxide; possibly in the range of 10 wppm to 1.0 wt %, individually.

The cleavage effluent also typically contains unreacted acid catalyst and hence at least a portion of the cleavage effluent may be neutralized with a basic material to remove or reduce the level of acid in the effluent.

Suitable basic materials include alkali metal hydroxides and oxides, alkali earth metal hydroxides and oxides, such as sodium hydroxide, potassium hydroxide, magnesium hydroxide, calcium hydroxide, calcium oxide, and barium hydroxide. Sodium and potassium carbonates may also be used, optionally, at elevated temperatures.

In various embodiments, the basic material comprises one or more of: a caustic exchange resin (e.g., sulfonic ion-exchange resin); ammonia or ammonium hydroxide; a basic clay, such as limestone, dolomite, magnesite, sepiolite, and olivine; an activated carbon and/or impregnated activated carbon; an anionic exchange resin, such as a weakly basic ion exchange resin having a styrene-divinyl benzene polymer backbone and an amine functional structure selected from —N(CH$_3$)$_2$, —NRH or —NR$_2$, where R is a hydrogen or an alkyl group containing 1 to 20 carbon atoms; an amine polysiloxane functionalized with ethylenediamine; an organic basic material grafted on microporous or mesoporous metal oxides; other organo-inorganic solids, such as zeolites exchanged with a metal selected from the group of lithium, sodium potassium, rubidium, cesium, calcium, barium, strontium, and radium; an oxide of Group III of the Periodic Table of Elements treated with a metal selected from lithium, potassium, sodium, rubidium, and cesium; a supported or solid alkali, alkaline-earth metal or organometallic; a magnesium silicate generally derived from the interaction of a magnesium salt and soluble silicate; a salt with basic hydrolysis such as sodium acetate, sodium bicarbonate, sodium phenate and sodium carbonate; and amine(s), such as a primary, secondary, or tertiary aliphatic amines or aromatic amines, e.g., anilines, n-butyl amine, heterocyclic amines, such as pyridines, piperidines, piperazines, tri-ethyl amine, aliphatic or aromatic diamines, and alkanolamines In particular, amines in the form of their salts with weak organic acids may be used. Conveniently, the basic material is a diamine, such as 2-methylpentamethyenediamine or hexamethylenediamine, which are commercially available from Invista S.à r.l. Corporation under the trade designations DYTEK™ A and DYTEK™ HMD.

Suitable solid basic materials include: basic metal oxide families; alkali on metal oxides; alkaline-earth on metal oxides; alkali and alkaline-earth zeolites; transition metals, rare earth, and higher valency oxides; hydrotalcites, calcined hydrotalcites, and spinels, specifically hydrotalcites treated with an alkali metal selected from lithium, potassium, sodium, rubidium, cesium, and combinations thereof; perovskites; and beta-aluminas In one embodiment, the basic material is one or more of the hindered amines described in U.S. Pat. No. 6,201,157. It will be understood that the basic material may be added in the anhydrous state or may be an aqueous solution of any of the foregoing basic materials, particularly the metal hydroxides and salts with basic hydrolysis.

Conveniently, any liquid basic material employed in the neutralization, such as an amine or diamine as has been discussed, has a relatively low volatility, with a normal boiling point temperature above that of cyclohexylbenzene, such that it will tend to remain in the bottoms product in subsequent fractionation operations that may be conducted on any portion of the treated cleavage effluent that may contain such liquid basic material.

The conditions at which the neutralization reaction is effected vary with the acid catalyst and basic material employed. Suitable neutralization conditions include a temperature of at least 30° C., or at least 40° C., or at least 50° C., or at least 60° C., or at least 70° C., or at least 80° C., or at least 90° C. Other suitable neutralization conditions include a temperature of no greater than 200° C., or no greater than 190° C., or no greater than 180° C., or no greater than 170° C., or no greater than 160° C., or no greater than 150° C., or no greater than 140° C., or no greater than 130° C., or no greater than 120° C., or no greater than 110° C., or no greater than 100° C. In various embodiments, the neutralization conditions include a temperature that is reduced from cleavage reaction conditions, for example, the temperature may be 1° C., or 5° C., or 10° C., or 15° C., or 20° C., or 30° C., or 40° C. lower than the temperature of the cleavage reaction.

Suitable neutralization conditions may include a pressure of about 1 psig to about 500 psig (5 kPa to 3450 kPa, gauge), or about 10 psig to 200 psig (70 kPa, gauge to 1380 kPa, gauge) such that the treated cleavage effluent is completely or predominantly in the liquid phase during the neutralization reaction.

In various embodiments, at least a portion of the cleavage effluent (such as the neutralized cleavage effluent) is fractionated to produce a first fraction richer in cyclohexanone than the cleavage effluent stream and a second fraction richer in phenol and depleted in cyclohexanone as compared with the cleavage effluent stream. As used herein, "richer in" means that the stream contains a higher wt % of the named component than a comparative stream. For example, "a first fraction richer in cyclohexanone than the cleavage effluent stream" means that the first fraction has a certain weight percent of cyclohexanone based upon total weight of the first fraction, and the cleavage effluent stream has a certain weight percent of cyclohexanone based upon total weight of the cleavage effluent stream. The wt % of the cyclohexanone in the first fraction is greater than the wt % of cyclohexanone in the cleavage effluent stream.

Similarly, "depleted in" means that the stream contains a lower wt % of the named component than a comparative stream. For example, "a first fraction depleted in cyclohexanone as compared with the cleavage effluent stream" means that the first fraction has a certain weight percent of cyclohexanone based upon total weight of the first fraction and the cleavage effluent stream has a certain weight percent of cyclohexanone based upon total weight of the cleavage effluent stream. The wt % of the cyclohexanone in the first fraction is less than the wt % of cyclohexanone in the cleavage effluent stream.

Since the weight ratio of phenol to cyclohexanone in the cleavage effluent stream portion is normally less than or equal to azeotropic ratio of 2.57:1, such as about 0.7:1 to about 1.5:1, this fractionation of the neutralized cleavage effluent can normally be effected by simple distillation, that is, without the use of the solvent employed in extractive distillation.

In various embodiments, the fractionation employed to produce the first fraction and second fraction takes place in a series of distillation column operations. For example, one may initially separate from the cleavage effluent, components of a higher boiling point (lower volatility) than the phenol-cyclohexanone azeotrope (e.g., cyclohexylbenzene, phenyl-cyclohexanone), then separate from that "tailed" cleavage effluent components with a lower boiling point (higher volatility) than cyclohexanone (e.g., methylcyclopentanone, pentanal, hexanal, and water). Then the first fraction and second fraction may be generated from that resultant portion of cleavage product having had those lower volatility and higher volatility components removed.

The distillation column producing the first fraction and the second fraction may be operated at a pressure of no greater than 300 mm Hg at 0° C. absolute (40 kPa, absolute), 200 mm Hg at 0° C. absolute (26.6 kPa, absolute), or 100 mm Hg at 0° C. absolute (13.3 kPa, absolute), or 60 mm Hg at 0° C. absolute (8 kPa, absolute). The temperatures will be autogenous at the selected operating pressures depending upon the composition of the at least a portion of the cleavage product containing phenol and cyclohexanone selected as feed to the distillation column, generally ranging from at least 60° C. in the overhead to no greater than 170° C. in the bottoms, or at least 70° C. in the overhead to no greater than 160° C. in the bottoms. Remarkably, the azeotropic composition of cyclohexanone and phenol is about the same, 72 wt % phenol and 28 wt % cyclohexanone, over a very wide range of conditions, from 100° C. to 225° C. and the associated autogeneous pressures, making the invention particularly robust.

Conveniently, the distillation column(s) used to produce the first fraction and the second fraction employ simple distillation of the components, that is, the fractional distillation method does not employ a solvent introduced to the column to facilitate the separation of phenol and cyclohexanone. Said another way, conveniently the separating is not what is generally termed an extractive distillation. Such uses of solvents for extractive distillation require an additional column to process the remaining stream for the recovery and reuse of such solvents.

The first fraction typically comprises no more than 1000 wppm, or no more than 500 wppm, or no more than 50 wppm, or no more than 5 wppm, or no more than 1 wppm by weight of phenol. In addition to phenol and cyclohexanone, the first fraction may comprise one of more of the following (based upon the total weight of the first fraction): p1 It may include no greater than 400 wppm, or no greater than 200 wppm, or no greater than 100 wppm, or no greater than 50 wppm, or no greater than 10 wppm, or no greater than 1 wppm cyclohexanol.

It may include no greater than 400 wppm, or no greater than 200 wppm, or no greater than 100 wppm, or no greater than 50 wppm, or no greater than 10 wppm, or no greater than 1 wppm methylcyclopentanone.

It may include no greater than 400 wppm, or no greater than 200 wppm, or no greater than 100 wppm, or no greater than 50 wppm, or no greater than 10 wppm, or no greater than 1 wppm cyclohexenone.

It may include no greater than 400 wppm, or no greater than 200 wppm, or no greater than 100 wppm, or no greater than 50 wppm, or no greater than 10 wppm, or no greater than 1 wppm 2-hydroxycyclohexanone.

It may include no greater than 400 wppm, or no greater than 200 wppm, or no greater than 100 wppm, or no greater than 50 wppm, or no greater than 10 wppm, or no greater than 1 wppm pentanal.

It may include no greater than 400 wppm, or no greater than 200 wppm, or no greater than 100 wppm, or no greater than 50 wppm, or no greater than 10 wppm, or no greater than 1 wppm hexanal.

It may include no greater than 1000 wppm, or no greater than 400 wppm, or no greater than 200 wppm, or no greater than 100 wppm, or no greater than 50 wppm, or no greater than 10 wppm, or no greater than 1 wppm water.

The first fraction is recovered for use as saleable cyclohexanone, either directly or after further purification, and may constitute the only cyclohexanone produced by the process. It is of course also possible to dehydrogenate this cyclohexanone to produce additional phenol in the manner discussed below.

It is to be appreciated that, not only is the first fraction produced by the present process a useful cyclohexanone product composition, but also it is very different from cyclohexanone typically produced by conventional methods, e.g., the cyclohexane oxidation process. The chemistry associated with cyclohexylbenzene as a starting material in the instant process provides contaminants potentially present in a cyclohexanone product composition that are of a markedly different type and concentration than conventional methods. The contaminants, per se, in the novel cyclohexanone product composition may be less problematic in further processing, e.g., to caprolactam, and/or because of their lower volatility compared to conventional methods, they may be present in lower concentrations compared to the cyclohexanone product composition of conventional methods. Finally, providing a second fraction with weight ratio of phenol to cyclohexanone no greater than 2.5, leaving an appreciable amount of cyclohexanone in the second fraction above the azeotrope, provides a first fraction with a low amount of contaminants having a very close or lower volatility than cyclohexanone, but the economics of the process do not suffer from the incomplete recovery of cyclohexanone because it will eventually be transformed into valuable phenol product through oxygenate dehydrogenation.

In one embodiment, there is a novel cyclohexanone product composition comprising at least 99.000 wt % cyclohexanone, at least 0.1 wppm and no greater than 100 wppm cyclohexanol, and at least 0.1 wppm and no greater than 10 wppm of at least one component, or of each of any combination of components selected from the group consisting of cyclohexanedione and hydroxycyclohexanone. The wt %s are based upon the total weight of the cyclohexanone product composition. In alternative embodiments, there is no greater than 100 wppm, or 50 wppm, or 10 wppm cyclohexanol. Conveniently, there is at least 99.500 wt %, 99.900 wt %, or 99.990 wt % cyclohexanone.

In other embodiments, there is a cyclohexanone product composition comprising at least 99.000 wt % cyclohexanone, at least 0.1 wppm and no greater than 400 wppm cyclohexanol, and at least 0.1 wppm and no greater than 100 wppm of at least one component, or of each of any combination of components selected from the group consisting of cyclohexanedione and hydroxycyclohexanone. The wt %s are based upon the total weight of the cyclohexanone product composition. In alternative embodiments, there is no greater than 50 wppm, or 10 wppm cyclohexanol. Conveniently, there is at least 99.500 wt %, 99.900 wt %, or 99.990 wt % cyclohexanone.

In other embodiments, there is a cyclohexanone product composition comprising at least 99.000 wt % cyclohexanone, at least 0.1 wppm and no greater than 100 wppm cyclohexanol, and at least 0.1 wppm and no greater than 3 wppm, or at least 0.1 wppm and no greater than 1 wppm of at least one component, or of each of any combination of components selected from the group consisting of cyclohexanedione and hydroxycyclohexanone. The wt %s are based upon the total weight of the cyclohexanone product composition. In alternative embodiments, there is no greater than 50 wppm, or 10 wppm cyclohexanol. Conveniently, there is at least 99.500 wt %, 99.900 wt %, or 99.990 wt % cyclohexanone.

In various embodiments, any of the cyclohexanone product compositions discussed herein may further comprise at least 0.1 wppm and no greater than 100 wppm, or 0.1 wppm and no greater than 10 wppm, or 0.1 wppm and no greater than 1 wppm each of cyclohexenone, hexanal, and methycyclopentanone.

Any of the cyclohexanone product compositions discussed herein may additionally comprise at least 0.1 wppm and no greater than 1000 wppm water, or even at least 0.1 wppm and no greater than 150 wppm water. Water may be measured, for example, by method DIN 51777/Part 1.

Also, any of the cyclohexanone product compositions discussed herein typically contain less than 1 wppm and generally no measurable concentration, using a gas chromatograph with a Carbowax column, of one or more of the components selected from the group consisting of methylcyclopentenone, methylcyclopentenal, cyclohexenone, cyclohexenol, phenol, butylcyclohexylether, pentylcyclohexane, cyclohexyl acetate, pentanal, valeric acid, and butyric acid. These components, typically produced by conventional methods, are particularly problematic in further processing of a cyclohexanone product composition, and are virtually non-existent in the method of the present invention, for example, they will be below the detectable limit in a gas chromatographic measurement technique specifically tailored and calibrated for those components. The concentration ranges of components in a cyclohexanone product composition of the instant invention, such as those in the aforementioned group, may be similarly measured by a gas chromatograph technique with a Carbowax column, tailored and calibrated for such components.

Finally, any of the cyclohexanone product compositions discussed herein may have acceptable or exceptional quality according to any industry standard specifications. These specifications may include, for example, Pt—Co color of 20 maximum, even as low as 5 (for example, by ASTM D209); free acidity as formic acid of 0.01 wt % maximum (for example, by ASTM D1613); density at 20 OC of 0.946+/− 0.002 g/cm3 (for example, by DIN 51757/Method D); distillation range (ASTM) of 1.8° C. maximum including 155.65° C.; refractive index N of 1.4480-1.4490; and a very low content of metals, such as Chloride 0.8 wppm maximum, Phosphate 1 wppm maximum, Aluminum 100 wppb maximum, Antimony 100 wppb maximum, Arsenic 100 wppb maximum, Boron 100 wppb maximum, Calcium 100 wppb maximum, Chromium 100 wppb maximum, Copper 100 wppb maximum, Gold 100 wppb maximum, Iron 100 wppb maximum, Lead 100 wppb maximum, Magnesium 100 wppb maximum, Manganese 100 wppb maximum, Nickel 100 wppb maximum, Potassium 100 wppb maximum, Sodium 100 wppb maximum, Tin 100 wppb maximum, Titanium 100 wppb maximum, and Zinc 100 wppb maximum.

The second fraction is composed mainly of phenol and cyclohexanone, in which the weight ratio of phenol to cyclohexanone is typically about 2.0 to about 2.5. The second fraction may include other components in the cleavage effluent of a lower boiling point than the phenol-cyclohexanone azeotrope but of a higher boiling point than cyclohexanone, for example, cyclohexeneone, 2-hydroxycyclohexanone. Conveniently, the second fraction is substantially free, that is, contains no more than 400 wppm, or no more than 200 wppm, or no more than 100 wppm, or no more than 50 wppm, or no more than 10 wppm, or no more than 1 wppm of components in the cleavage effluent of a higher boiling point than the phenol-cyclohexanone azeotrope, for example, cyclohexylbenzene, bicyclohexane, phenyl cyclohexanone. Similarly, the second fraction is substantially free, that is, contains no more than 400 wppm, or no more than 200 wppm, or no more than 100 wppm, or no more than 50 wppm, or no more than 10 wppm, or no more than 1 wppm of components in the cleavage effluent of a lower boiling point than cyclohexanone, for example, methylcyclopentanone.

The second fraction is contacted with a dehydrogenation catalyst in a dehydrogenation reaction zone under dehydrogenation conditions effective to convert at least a portion of the cyclohexanone in said second fraction portion into phenol and cyclohexanol and produce a product stream comprising phenol, cyclohexanol and cyclohexanone, and a hydrogen stream. The hydrogen stream is removed from the product stream and, after removal of any entrained impurities, may be recycled to the benzene hydrogenation step.

Any dehydrogenation catalyst effective to selectively convert cyclohexanone and cyclohexanol to phenol can be used in the dehydrogenation reaction zone. One example of such a catalyst comprises (i) a support; (ii) a hydrogenation-dehydrogenation component comprising at least one metal or compound thereof selected from Groups 6 to 10 of the Periodic Table of Elements, especially platinum; and (iii) a promoter comprising at least one metal or compound thereof selected from Group 1 of the Periodic Table of Elements, especially potassium. Another example of a suitable catalyst comprises (i) a support; (ii) a dehydrogenation component comprising at least one metal or compound thereof selected from Groups 6 to 10 of the Periodic Table of Elements, especially platinum; and (iii) tin or a tin compound.

The tin or tin compound may be present in an amount of greater than about 0.01 to about 0.25 wt %, or about 0.02 wt % to about 0.25 wt %, or about 0.03 wt % to about 0.25 wt %, or about 0.04 wt % to about 0.20 wt %, or about 0.05 wt % to about 0.20 wt %, or about 0.05 wt % to about 0.15 wt %, 0.07 wt % to about 0.1 wt % of tin based upon the total weight of the catalyst composition, with ranges from any lower limit to any upper limit being contemplated. In other embodiments, the tin or tin compound may be replaced by another metal component selected from Group 14 of the Periodic Table of Elements.

Suitable conditions for the dehydrogenation step comprise a temperature of about 250° C. to about 500° C. and/or a pressure of about 0.01 atm to about 20 atm (1 kPa to 2000 kPa), such as a temperature of about 300° C. to about 450° C. and a pressure of about 1 atm to about 3 atm (100 kPa to 300 kPa). The weight hourly space velocity may be about 0.2 to 50 hr$^{-1}$, and the hydrogen to cyclohexanone-containing feed molar ratio of about 2 to about 20. To improve catalyst stability, hydrogen may be co-fed to the dehydrogenation reaction, typically such that the molar ratio of hydrogen to all of cyclohexanone, cyclohexanol and phenol in the dehydrogenation feed is about 0:1 to about 4:1. This co-fed hydrogen may be recycled within the dehydrogenation, for example using a portion of the hydrogen stream, or from another source, for example from a third party supplier.

The reactor configuration used for the dehydrogenation process generally comprises one or more fixed bed reactors containing the dehydrogenation catalyst. Provision can be made for the endothermic heat of reaction, preferably by multiple adiabatic beds with interstage heat exchangers. The temperature of the reaction stream drops across each catalyst bed, and then is raised by the heat exchangers. Preferably, 3 to 5 beds are used, with a temperature drop of about 30° C. to about 100° C. across each bed. Preferably, the last bed in the series runs at a higher exit temperature than the first bed in the series.

The product stream from dehydrogenation is fed to a fractionation system to recover a phenol-containing stream from the product stream, and to leave a residual stream comprising cyclohexanol and cyclohexanone. Provided the weight ratio of phenol to cyclohexanone in the product stream is greater than 2.57, recovery of the phenol-containing stream from the product stream can be achieved by simple distillation. The resultant phenol-containing stream typically contains a small amount, say at least 0.5 wppm, or at least 1 wppm of cyclohexanone and cyclohexanol combined, but generally contains no more than 1.0 wt %, or no more than 0.5 wt %, or no more than 1000 wppm, or no more than 500 wppm, or no more than 50 wppm, or no more than 5 wppm of cyclohexanone and cyclohexanol combined. In addition, the phenol-containing stream may contain at least 0.5 wppm, or at least 1 wppm of butylbenzene and/or pentylbenzene, but generally contains no more than 10 wppm, or no more than 5 wppm of butylbenzene and/or pentylbenzene.

The residual stream is then contacted with a dehydrogenation catalyst in a dehydrogenation reaction zone under dehydrogenation conditions effective to convert at least a portion of the cyclohexanol and cyclohexanone in said residual stream portion into phenol and produce a further product stream comprising phenol, cyclohexanone and cyclohexanol, and a further hydrogen stream. Conveniently, the second fraction and the residual stream are dehydrogenated in the same dehydrogenation reaction zone using the same dehydrogenation catalyst, providing a single product stream and a single hydrogen stream, and the single product stream is fed to a common fractionation system to recover a single phenol-containing stream from the single product stream, and to leave a single residual stream comprising cyclohexanol and cyclohexanone.

By repeating the cycle of recovering the phenol and dehydrogenating the cyclohexanone in the second fraction it is possible to convert at least 90 wt %, or at least 95.0 wt %, or at least 99.0 wt %, or at least 99.5 wt % of the cyclohexanone in the second fraction to phenol.

The method of the present invention may provide for recovery of unreacted cyclohexanone from the dehydrogenation product stream; however, this cyclohexanone material will contain byproducts of a different concentration, or even type, than those described above. In particular, a cyclohexanone product composition derived at least in part from the dehydrogenation product stream may contain at least some of any isomer of methylcyclopentenone, or at least some of any isomer of cyclohexenol, or both.

In one embodiment, there is a novel cyclohexanone product composition comprising at least 99.000 wt % cyclohexanone, at least 0.1 wppm and no greater than 400 wppm cyclohexanol, and at least 0.1 wppm and no greater than 100 wppm of at least one component, or of each of any combination of components selected from the group consisting of methylcyclopentenone, cyclohexenol, cyclohexanedione, and hydroxycyclohexanone. In alternative embodiments, there is no greater than 200 wppm wppm cyclohexanol. Conveniently, there is at least 99.500 wt % or 99.900 wt % cyclohexanone.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon 6 and nylon 6,6.

The phenol produced through the processes disclosed herein may be used, for example, to produce phenolic resins, bisphenol A, ε-caprolactam, adipic acid, and/or plasticizers.

The invention will now be more particularly described with reference to the accompanying drawings.

Thus, FIG. 1 is a schematic view of one embodiment of a process for producing phenol and cyclohexanone from cyclohexylbenzene. In this process, a feedstock comprising cyclohexylbenzene is fed by line 102 to an oxidation reactor 106, which also receives an oxygen-containing stream, such as air, via line 104. Conditions within oxidation reactor 106 are such that at least a portion of the cyclohexylbenzene is oxidized to produce cyclohexylbenzene hydroperoxide, and in particular to produce cyclohexyl-1-phenyl-1-hydroperoxide. As the oxidation reaction continues, oxygen in the reactor 106 is depleted and an oxygen depleted stream is removed from oxidation reactor 106 via line 108. When the oxygen-containing stream in line 104 is air, the oxygen depleted stream in line 108 is typically enriched in nitrogen. When the oxidation reaction is conducted at or near atmospheric pressure, the oxygen-depleted stream in line 108 may also contain lower volatility byproducts of the oxidation reaction, such as water, along with minor amounts of cyclohexylbenzene, among other components that may be vapor under the conditions in oxidation reactor 106. In an operation not shown in FIG. 1, the oxygen depleted stream in line 108 may be further processed to recover the cyclohexylbenzene, remove water, and otherwise make the cyclohexylbenzene fit for recycle as feed to oxidation reactor 106, and make other streams suitable for other uses or disposal.

The oxidation effluent stream from the oxidation reactor 106, including cyclohexylbenzene hydroperoxide, is fed by line 110, along with a cleavage catalyst, such as sulfuric acid, in line 112 to a cleavage reactor 114. Conditions in the cleavage reactor 114 are such that cyclohexylbenzene hydroperoxide in the oxidation effluent stream is decomposed to produce phenol and cyclohexanone in a respective weight ratio of less than 2.57. The cleavage effluent stream from the cleavage reactor 114 is fed by line 116 to a separation device, for example, a conventional fractionation column 118. Fractionation column 118 is operated to divide the cleavage effluent into a first fraction composed of cyclohexanone (including, for example, no greater than 1000 wppm of phenol) that is removed in line 120 as an overhead of the fractionation column 118, and a second fraction including phenol and cyclohexanone that is removed in line 122 as a bottoms product of the fractionation column 118. The second fraction in line 122 has a phenol to cyclohexanone weight ratio that is greater than that of the cleavage effluent in line 116.

The second fraction containing phenol and cyclohexanone is fed by line 122 to a dehydrogenation reactor 124, along with a residual stream including cyclohexanone and cyclohexanol in line 134. The conditions in dehydrogenation reactor 124 are such that some of the cyclohexanone in the second fraction, and some of the cyclohexanone and cyclohexanol in the residual stream are converted to additional phenol, and also to hydrogen. A hydrogen stream is removed from the reactor 124 via line 126.

Under the dehydrogenation conditions in dehydrogenation reactor 124, a thermodynamic equilibrium exists between unconverted cyclohexanone and cyclohexanol. Thus, the product stream includes phenol, cyclohexanone, and cyclohexanol and is removed from the oxygenate dehydrogenation reactor 124 in line 128. The product stream in line 128 will include a lower proportion of cyclohexanone and cyclohexanol and a higher proportion of phenol than that of the combined material introduced to the dehydrogenation reactor 124.

The product stream in line 128 is fed to a further separation device, for example, a second fractionation column 130, which is operated to recover from the product stream a phenol-containing stream including no greater than 1.0 wt % of cyclohexanone and cyclohexanol combined. The phenol-containing stream is removed as an overhead of the second fractionation column 130 in line 132 to leave a residual stream including cyclohexanone and cyclohexanol, and optionally phenol, that is removed as a bottoms product of the second fractionation column 130 in line 134. The residual stream has a phenol to cyclohexanone weight ratio that is lower than that of the product stream in line 128 from dehydrogenation. As noted earlier, the residual stream is fed via line 134 to the oxygenate dehydrogenation reactor 124, and in this manner most or all of the cyclohexanone not recovered from the cleavage effluent in line 120 may efficiently be converted to and recovered as phenol product in line 132.

Fractionation column 130 may be any fractional distillation system suitably correlated to conduct a separation of a phenol product including no greater than 1.0 wt % wppm cyclohexanone and cyclohexanol combined from a stream including phenol, cyclohexanone and cyclohexanol. Conveniently, fractionation column 130 is an extractive distillation column.

Figure 2:
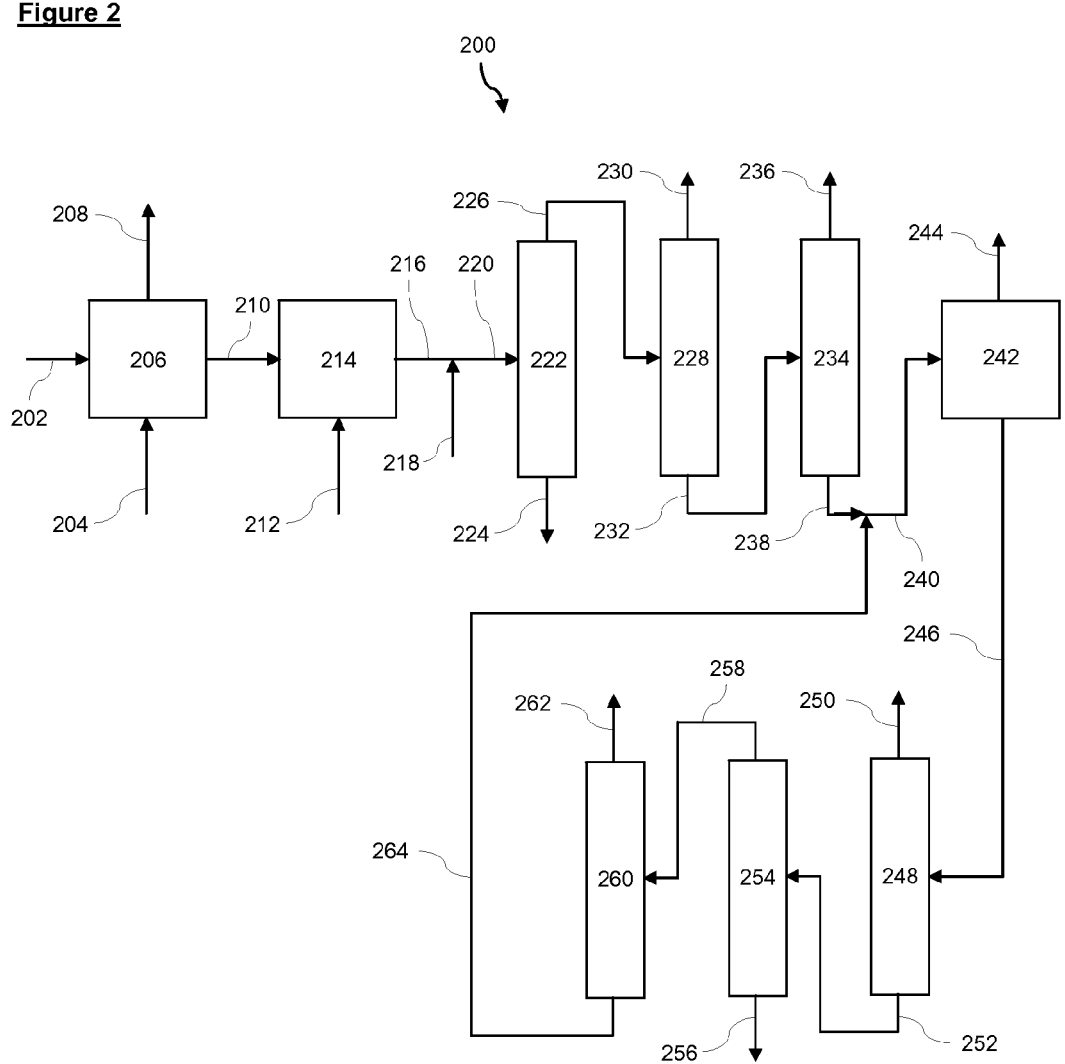
FIG. 2 is a schematic view of a more detailed process for producing phenol and cyclohexanone from cyclohexylbenzene in accordance with a second example of the present invention and including additional intermediate purification steps.

FIG. 2 is a schematic view of another embodiment of a process for producing phenol and cyclohexanone from cyclohexylbenzene. A feedstock comprising cyclohexylbenzene is provided by line 202 to an oxidation reactor 206, which also receives a stream comprising oxygen, conveniently air, by way of line 204. Conditions within oxidation reactor 206 are such that at least a portion of the cyclohexylbenzene is oxidized to produce an oxidation effluent stream comprising cyclohexylbenzene hydroperoxide, which exits the oxidation reactor 206 through line 210, while an oxygen-depleted stream is removed from oxidation reactor 206 via line 208.

The oxidation effluent stream from the oxidation reactor 206, including cyclohexylbenzene hydroperoxide and unreacted cyclohexylbenzene, is fed by line 210, along with sulfuric acid as a catalyst in line 212, to a cleavage reactor 214. Conditions in the cleavage reactor 214 are such that cyclohexylbenzene hydroperoxide in the oxidation effluent is decomposed to produce a cleavage effluent stream in which phenol and cyclohexanone are in a respective weight ratio of less than 2.57. The cleavage effluent stream is removed from the cleavage reactor 214 in line 216 and, since the cleavage effluent stream contains residual sulfuric acid as well as phenol and cyclohexanone, it is initially mixed with an amine, such as 2-methylpentane-1,5 diamine in line 218. The amine neutralizes and complexes the sulfuric acid in the cleavage effluent stream to produce amine-sulfuric acid salt(s), that are conveniently completely soluble in the balance of the neutralized cleavage effluent and further have a relatively low volatility compared to cyclohexylbenzene. In one embodiment, an excess of an amine compound is supplied in line 218 beyond the stoichiometric neutralization of the sulfuric acid in line 216, to give the neutralized cleavage effluent stream a more basic character that promotes conversions of certain contaminant byproducts.

The neutralized cleavage effluent stream is fed by line 220 to a first separation device, for example, first fractionation column 222, which is operated to separate from the neutralized cleavage effluent a first overhead product comprising phenol, cyclohexanone, and components of a lower boiling point than the phenol-cyclohexanone azeotrope. Conveniently, the first overhead product is substantially free of cyclohexylbenzene and exits the first fractionation column 222 in line 226. The portion of the neutralized cleavage effluent stream remaining after separation of the first overhead product is a third fraction that comprises cyclohexylbenzene and components of a higher boiling point than cyclohexylbenzene and is removed as a bottoms product of first fractionation column 222 in line 224. Conveniently, the third fraction in line 224 is very low in the cyclohexanone-phenol azeotrope composition, for example, comprising no greater than 1.0 wt %, or no greater than 0.1 wt %, or even no greater than 100 wppm of phenol and cyclohexanone combined, and may be made available for further processing and eventually made suitable for recycle as feedstock to the oxidation reactor 206.

The first overhead product is supplied by line 226 to a second separation device, for example, second fractionation column 228, which is operated to form a first light product that is removed as an overhead of second fractionation column 228 in line 230. The first lights product contains water and other light by-products of the oxidation process such as pentanal, hexanal, and methylcyclopentanone. The first light product includes a small amount of cyclohexanone, for example, at least about 0.1 wt % but no greater than 5.0 wt %, or no greater than 2.0 wt %, cyclohexanone to ensure sufficient removal of light components. Second fractionation column 228 is further operated to form a second bottoms product that is removed from second fractionation column 228 in line 232. Conveniently, the second bottoms product in line 232 is composed mainly of phenol and cyclohexanone and is very low in light components, for example, water, pentanal, hexanal, and methylcyclopentanone, typically comprising no greater than 1.0 wt %, or no greater than 0.1 wt %, or even no greater than 100 wppm of water, pentanal, hexanal, and methylcyclopentanone combined.

The second bottoms product is fed by line 232 to a third separation device, for example, a third fractionation column 234, which is operated to separate the second bottoms product into a first fraction which includes cyclohexanone and no more than 1000 wppm of phenol and a second fraction that is richer in phenol and depleted in cyclohexanone as compared with the second bottoms product. The first fraction is removed as an overhead from the third fractionation column 234 in line 236, while the second fraction is removed as a bottoms product via line 238. The second fraction in line 238 is combined with a residual stream including cyclohexanone and cyclohexanol in line 264 and fed by line 240 to an oxygenate dehydrogenation reactor 242.

In the oxygenate dehydrogenation reactor 242, the mixture of the second fraction and the residual stream is exposed to oxygenate dehydrogenation conditions, under which some of the cyclohexanone and cyclohexanol contained therein are converted to additional phenol, and also hydrogen. A gaseous hydrogen stream is removed from oxygenate dehydrogenation reactor 242 in line 244, while a liquid dehydrogenation product stream is removed from reactor 242 in line 246.

Under the oxygenate dehydrogenation conditions existing in oxygenate dehydrogenation reactor 242, a thermodynamic equilibrium exists between unconverted cyclohexanone and cyclohexanol. Thus, the product stream in line 246 includes phenol, cyclohexanone and cyclohexanol but with a lower proportion of cyclohexanone and cyclohexanol and a higher proportion of phenol than the mixed second fraction and residual stream feed to the dehydrogenation reactor 242 in line 240. In one embodiment, the phenol to cyclohexanone weight ratio of the product stream in line 246 is at least 2.60.

The product stream in line 246 is provided to a fourth separation device, for example, a fourth fractionation column 248. The fourth fractionation column 248 is operated to separate from the product stream a second lights product that is removed as an overhead of column 248 in line 250. The second lights product typically includes components such as water, pentane, benzene, and toluene as may have been produced as byproducts of the oxygenate dehydrogenation reaction conducted in oxygenate dehydrogenation reactor 242. Conveniently, the second lights product includes only a low concentration of cyclohexanone and phenol, for example, no greater than 5.0 wt %, or 2.0 wt %, or 1.0 wt %, or 100 wppm of phenol and cyclohexanone combined, and may be made available for further processing, possibly for recovery of benzene suitable for use in producing cyclohexylbenzene, or for use as a fuel. Fourth fractionation column 248 is further operated to form a fourth bottoms product that is removed from the column 248 in bottoms line 252. The fourth bottoms product comprises phenol, cyclohexanone, and cyclohexanol in line 252 and is very low in light components, for example water, pentane, benzene, and toluene, typically comprising no greater than 1.0 wt %, or 0.1 wt %, or 100 wppm, or 10 wppm of such as water, pentane, benzene, and toluene combined.

The fourth bottoms product is supplied by line 252 to a fifth separation device, for example, fifth fractionation column 254. The fifth fractionation column 254 is operated to separate the fourth bottoms product into a fifth overhead product and a fifth bottoms product. The fifth overhead product includes phenol, cyclohexanone and cyclohexanol and is removed from the fifth fractionation column 254 in line 258. Conveniently, the fifth overhead product in line 258 includes a low concentration of components with a higher boiling point than the cyclohexanone-phenol azeotrope, for example, cyclohexylbenzene, dicyclohexyl ether, biphenyl, diphenyl ether, 2-butyl cyclohexanone, cyclohexyl phenyl ether, 2-phenyl phenol, dibenzofuran, 2-cyclohexyl phenol and 4-phenyl phenol, as may have been produced as byproducts of the oxygenate dehydrogenation reaction conducted in oxygenate dehydrogenation reactor 242. For example, the fifth overhead product may include, no greater than 1.0 wt %, or no greater than 0.5 wt %, or no greater than 0.1 wt %, or no greater than 100 wppm of such high boiling components, individually or all of them combined. The fifth bottoms product comprises most of the components with a higher boiling point than the cyclohexanone-phenol azeotrope and is removed from the fifth fractionation column 254 in line 256.

Conveniently, the fifth bottoms product contains no greater than 5.0 wt %, or no greater than 1.0 wt %, or no greater than 0.5 wt %, or no greater than 0.1 wt %, or no greater than 100 wppm of phenol, cyclohexanone, and cyclohexanol, individually or all of them combined.

In one embodiment, the fifth bottoms product in line 256 is used as a fuel, or otherwise used in applications outside the scope of the present process. Due to the presence of dicyclohexylether, which forms an azeotrope with cyclohexylbenzene in addition to having a boiling point within about 1° C. of cyclohexylbenzene, it is convenient that the fifth bottoms product be discarded and no attempt made to recover the cyclohexylbenzene, for example, for recycle as feed to oxidation.

The fifth overhead product is fed by line 258 to a sixth separation device, for example, sixth fractionation column 260, which is operated to separate the fifth overhead product into a phenol-containing stream and a residual stream which contains cyclohexanone and cyclohexanol and which is depleted in phenol. The phenol-containing stream includes no greater than 1.0 wt % of cyclohexanone and cyclohexanol combined and is recovered as an overhead of sixth fractionation column 260 in line 262 for further processing. The residual stream is removed as a bottoms product of sixth fractionation column 260 in line 264. In one embodiment, where as noted above the phenol to cyclohexanone weight ratio of the dehydrogenation product in line 246 is at least 2.60, which is in phenol excess of the azeotropic composition with cyclohexanone, sixth fractionation column 260 is a simple distillation column and need not employ any solvents or other means to break the azeotrope. Any phenol in excess of the phenol-cyclohexanone azeotrope may be straightforwardly recovered as the phenol-containing stream in line 262. The residual stream in line 264 has a phenol to cyclohexanone weight ratio that is lower than that of the product from dehydrogenation in line 246 but which will not be below the cyclohexanone-phenol azeotropic composition. As noted earlier, the residual stream in line 264 is recycled to the oxygenate dehydrogenation reactor 242, and in this manner most or all of the cyclohexanone not recovered from the neutralized cleavage effluent stream in line 220 as the first fraction in line 236 may efficiently be converted to and recovered as phenol-containing stream in line 262.

Figure 3:
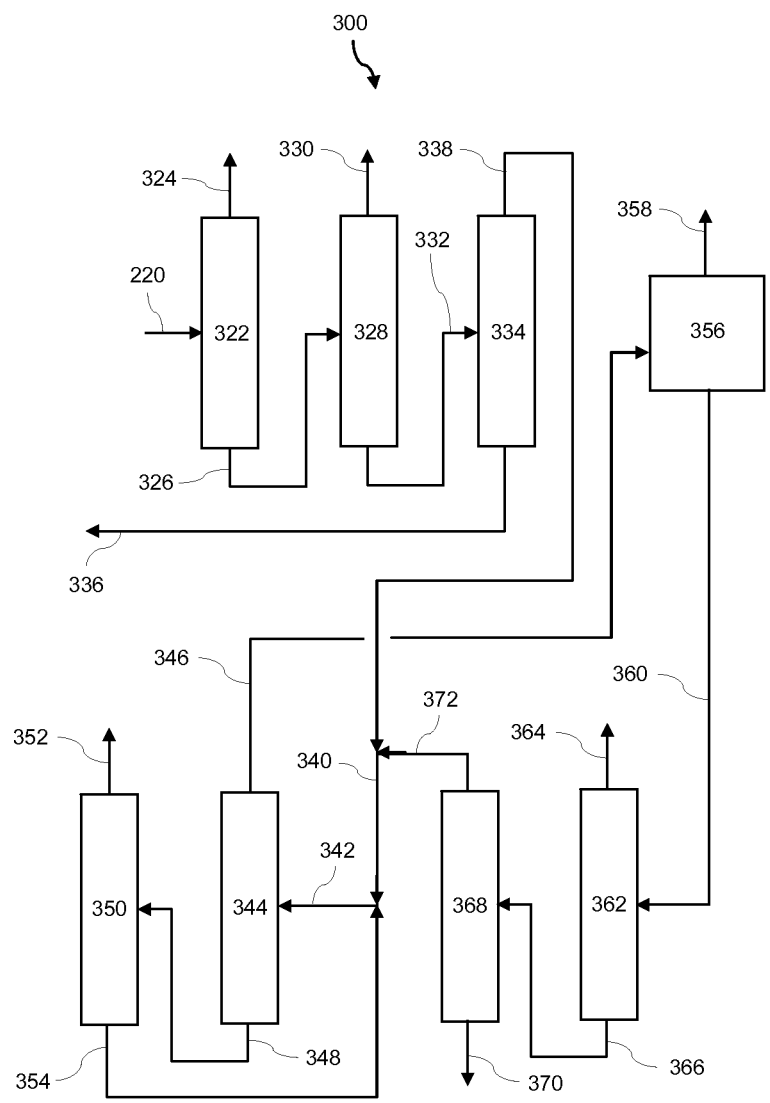
FIG. 3 is a schematic view of a modified version of the process shown in FIG. 2.

FIG. 3 is a schematic view of yet another embodiment of a process for producing phenol and cyclohexanone from cyclohexylbenzene. Referring now to FIG. 3, the neutralized cleavage effluent stream in line 220 as described for FIG. 2 is again supplied to a first separation device, for example, first fractionation column 322. However, in this case of FIG. 3, the first fractionation column 322 is operated to separate a first lights product comprising water, pentanal, hexanal, and methylcyclopentanone from the neutralized cleavage effluent. The first lights product includes a low amount of cyclohexanone, for example, no greater than 5.0 wt %, or no greater than 2.0 wt %, but at least about 0.1 wt % cyclohexanone to ensure sufficient removal of light components from the neutralized cleavage product. The first lights product is removed as an overhead of first fractionation column 322 in line 324. First fractionation column 322 is further operated to form from the neutralized cleavage effluent stream a first bottoms product comprising phenol and cyclohexanone that is removed from first fractionation column 322 in line 326. Conveniently, the first bottoms product in line 326 is very low in light components, for example, comprising no greater than 1.0 wt %, or no greater than 0.1 wt %, or even no greater than 100 wppm of water, pentanal, hexanal, and methylcyclopentanone combined.

The first bottoms product in line 326, derived from the cleavage effluent stream in line 220 and including phenol and cyclohexanone in a respective weight ratio of less than or equal to 2.57, is fed to a second separation device, for example, a second fractionation column 328. Second fractionation column 328 is operated to separate the first bottoms product into a first fraction including cyclohexanone and no greater than 1000 wppm of phenol that is removed in line 330 as an overhead of second fractionation column 328, and a second fraction including phenol and cyclohexanone that is removed in line 332 as a bottoms of second fractionation column 328. The second fraction is richer in phenol and depleted in cyclohexanone as compared with the cleavage effluent stream in line 220, and at least a portion of the cyclohexanone in the second fraction in line 338 will be provided to a dehydrogenation reaction zone in oxygenate dehydrogenation reactor 356, as discussed below.

The second fraction is supplied by line 332 to a third separation device, for example, third fractionation column 334, which is operated to divide the second fraction into a third overhead stream which includes phenol and cyclohexanone and which is substantially free of cyclohexylbenzene, and a third fraction comprising cyclohexylbenzene and components of a higher boiling point than cyclohexylbenzene. The third fraction is removed from third fractionation column 334 as a bottoms product via line 336 for further processing and recycle of the cyclohexylbenzene to the oxidation reactor. The third overhead stream, comprising cyclohexanone derived from the second fraction, is removed from third fractionation column 334 in line 338, and is combined with a fifth overhead stream including phenol, cyclohexanone, and cyclohexanol in line 372 (as described below), thus forming combined third and fifth overhead streams in line 340. In addition, these combined streams are further combined with a solvent recycle stream in line 354 (as described below) to form an extraction column feed in line 342.

The extraction column feed in line 342 is provided to a sixth separation device, for example, an extractive distillation column 344, which is operated to separate the extraction column feed into a combined second fraction and residual stream including cyclohexanone and cyclohexanol, and optionally phenol, and a sixth bottoms product including phenol and solvent. The combined second fraction and residual stream is removed as an overhead product from extractive distillation column 344 via line 346, includes cyclohexanone derived from the second fraction as processed through third fractionation column 334 and extractive distillation column 344, and includes cyclohexanone and cyclohexanol derived from the product stream as processed through fourth fractionation column 362, fifth fractionation column 368, and extractive distillation column 344. The combined second fraction and residual stream in line 346 conveniently contains no greater than 1.0 wt %, or no greater than 1000 wppm, or no greater than 100 wppm of solvent, since the solvent is likely to be decomposed when exposed to oxygenate dehydrogenation conditions. Also, the combined second fraction and residual stream residual stream conveniently contains at least 100 wppm, or at least 1000 wppm but no greater than 70.0 wt %, or no greater than 50.0 wt % of phenol. The amount of phenol in the combined second fraction and residual stream in line 346 is correlated to the desired operation of oxygenate dehydrogenation, and having a minimum amount of phenol ensures high removal of cyclohexanone and cyclohexanol from the sixth bottoms product in line 348, from which the phenol-containing stream will be obtained. The sixth bottoms product including phenol and solvent is removed from extractive distillation column 344 by way of line 348 and conveniently contains less than 1.0 wt % cyclohexanone and cyclohexanol combined relative to the total amount of phenol, cyclohexanone, and cyclohexanol in the sixth bottoms product (i.e., exclusive of solvent or any other component).

In one embodiment, the solvent employed in the extractive distillation column 344 is one known to effect the separation of phenol from cyclohexanone beyond the cyclohexanone-phenol azeotrope composition, allowing for near quantitative separation of the two components regardless of the phenol to cyclohexanone weight ratio in the extraction column feed, as noted in U.S. Pat. No. 2,265,939. Convenient solvents include, for example, 1,4-butanediol, 1,5-pentanediol, diethylene glycol, or triethylene glycol, which have a boiling point markedly higher than phenol, a negative deviation from Raoult's Law with phenol, i.e, they tend to draw phenol into the liquid phase, and a positive deviation from Raoult's Law with cyclohexanone, i.e., they tend to push cyclohexanone into the vapor phase.

The sixth bottoms product is supplied by line 348 to a seventh separation device, for example, solvent recovery column 350, which is operated to divide the sixth bottoms product into a phenol-containing stream including no greater than 1.0 wt % of cyclohexanone and cyclohexanol combined, and a solvent recycle stream. The solvent recycle stream is removed as a bottoms product of solvent recovery column 350 in line 354, and as noted earlier is returned to the extractive distillation column 344. Conveniently, the solvent recycle stream includes a small amount of phenol, for example, at least 100 wppm, or at least 1000 wppm but no greater than 5.0 wt %, or no greater than 1.0 wt %. Having a certain amount of phenol in the recycle solvent stream in line 354 ensures high recovery of the solvent for recycle use, and also a low amount of solvent in the phenol-containing stream, for example, no greater than 1.0 wt %, or no greater than 1000 wppm, or no greater than 10 wppm, or no greater than 1 wppm of solvent in the phenol-containing stream. The phenol-containing stream is removed as an overhead from solvent recovery column 350 in line 352 and recovered for further processing.

The combined second fraction and residual stream in line 346 is supplied to an oxygenate dehydrogenation reactor 356, where the combined second fraction and residual stream is exposed to oxygenate dehydrogenation conditions such that the cyclohexanone and cyclohexanol are converted to additional phenol, and also hydrogen. A hydrogen stream is removed from oxygenate dehydrogenation reactor 356 in line 358, while a product stream including phenol, cyclohexanone, and cyclohexanol is removed from oxygenate dehydrogenation reactor 356 in line 360. The product stream from dehydrogenation in line 360 will include a lower proportion of cyclohexanone and cyclohexanol and a higher proportion of phenol than the second overhead stream, although given the use of extractive distillation to separate phenol, the phenol to cyclohexanone weight ratio in the dehydrogenation product stream may vary widely.

The product stream is fed by line 360 to a fourth separation device, for example, fourth fractionation column 362, which is operated to divide the product from dehydrogenation into a second lights product, which is removed in line 364 as an overhead of fourth fractionation column 362, and a fourth bottoms product, which is removed from column 362 in line 366. The second lights product may include components such as water, pentane, benzene, and toluene as may have been produced as byproducts of the oxygenate dehydrogenation reaction conducted in oxygenate dehydrogenation reactor 356. Generally, the second lights product includes no more than 5.0 wt %, or no more than 2.0 wt %, or no more than 1.0 wt %, or no more than 100 wppm of phenol and cyclohexanone combined. The second lights product may be recovered for further processing, possibly for recovery of benzene suitable for use in producing cyclohexylbenzene, or for use as a fuel. The fourth bottoms product comprises mainly phenol, cyclohexanone, and cyclohexanol and is generally very low in light components, for example water, pentane, benzene, and toluene, comprising no more than 1.0 wt %, or no more than 0.1 wt %, or no more than 100 wppm, or no more than 10 wppm of such as water, pentane, benzene, and toluene combined.

The fourth bottoms product is fed by line 366 to a fifth separation device, for example, fifth fractionation column 368, which is operated to divide the fourth bottoms product into a fifth overhead product, which is removed from fifth fractionation column 368 in line 372 and, as discussed above, provided to the extractive distillation column 344, and a fifth bottoms product, which is removed from fifth fractionation column 368 by line 370. The fifth overhead product in line 372 is composed mainly of phenol, cyclohexanone, and cyclohexanol derived from the product, and has a low concentration of components with a higher boiling point than the cyclohexanone-phenol azeotrope, for example, cyclohexylbenzene, dicyclohexyl ether, biphenyl, diphenyl ether, 2-butyl cyclohexanone, cyclohexyl phenyl ether, 2-phenyl phenol, dibenzofuran, 2-cyclohexyl phenol, and 4-phenyl phenol, as may have been produced as byproducts of the oxygenate dehydrogenation reaction conducted in oxygenate dehydrogenation reactor 356. Typically, the third overhead product includes no more than 1.0 wt %, or no more than 0.5 wt %, or no more than 0.1 wt %, or no more than 100 wppm of such high boiling components, individually or all of them combined. The fifth bottoms product in line 370 is composed mainly of the high boiling by-products of the oxygenate dehydrogenation reaction and has a low concentration of phenol, cyclohexanone, and cyclohexanol, for example, no more than 5.0 wt %, or no more than 1.0 wt %, or no more than 0.5 wt %, or no more than 0.1 wt %, or no more than 100 wppm of phenol, cyclohexanone, and cyclohexanol, individually or all of them combined.

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for producing phenol, the process comprising:
   (a) cleaving cyclohexylbenzene hydroperoxide to produce a cleavage effluent stream comprising phenol and cyclohexanone in a weight ratio of phenol to cyclohexanone of about 0.7:1 to about 1.5:1;
   (b) fractionating at least a portion of the cleavage effluent stream to produce
      (i) a first fraction richer in cyclohexanone than said portion of the cleavage effluent stream, said first fraction comprising no more than 500 wppm phenol, 0.1 wppm to 400 wppm of cyclohexanol, and 0.1 wppm to 100 wppm of at least one of methylcyclopentanone, cyclohexenol, cyclohexanedione, and hydroxycyclohexanone, said wppm amounts based on the total weight of the first fraction; and
      (ii) a second fraction richer in phenol and depleted in cyclohexanone than said portion of the cleavage effluent stream, such that the weight ratio of phenol to cyclohexanone in said second fraction is about 2.0:1 to about 2.5:1;

(b-1) recovering the first fraction as a cyclohexanone product; and (c) contacting at least a portion of the second fraction with a dehydrogenation catalyst in a dehydrogenation reaction zone under dehydrogenation conditions effective to convert at least a portion of the cyclohexanone in said portion of the second fraction into phenol and cyclohexanol.

2. The process of claim 1, wherein said fractionating (b) is effected by distillation.

3. The process of claim 1, wherein the contacting (c) produces (i) a product stream comprising phenol, cyclohexanol, and cyclohexanone; and (ii) a hydrogen stream.

4. The process of claim 3, and further comprising:

(d) recovering a phenol-containing stream from said product stream to leave a residual stream comprising cyclohexanol and cyclohexanone; and (e) contacting at least a portion of the residual stream with a dehydrogenation catalyst in a dehydrogenation reaction zone under dehydrogenation conditions effective to convert at least a portion of the cyclohexanol and cyclohexanone in said portion of the residual stream into phenol and produce (i) a further product stream comprising phenol, cyclohexanone, and cyclohexanol; (ii) and a further hydrogen stream.

5. The process of claim 4, wherein said phenol-containing stream recovered in (d) contains no more than 1 wt % of cyclohexanone and cyclohexanol combined, the wt % based upon the total weight of the phenol-containing stream.

6. The process of claim 5, wherein the weight ratio of phenol to cyclohexanone in said product stream is greater than 2.57 and said phenol-containing stream is recovered from said product stream by simple distillation.

7. The process of claim 4, wherein said portion of the residual stream in (e) and said portion of the second fraction in (b) are contacted with a dehydrogenation catalyst in the same dehydrogenation reaction zone.

8. The process of claim 4, and further comprising:

(f) recycling at least a portion of said further product stream to said recovering (d); and (g) repeating said recovering (d), said contacting (e) and said recycling (f) to convert at least 90 wt % of the cyclohexanone in said second fraction to phenol, the wt % based upon the total weight of said second fraction.

9. The process of claim 1, wherein the dehydrogenation catalyst comprises (i) a support; (ii) a dehydrogenation component comprising at least one metal or compound thereof selected from Groups 6 to 10 of the Periodic Table of Elements; and (iii) tin or a tin compound, wherein the tin is present in an amount of 0.01 wt % to about 0.25 wt %, the wt % based upon the total weight of the dehydrogenation catalyst.

10. The process of claim 1, wherein the dehydrogenation conditions comprise a temperature of about 250° C. to about 500° C. and a pressure of about 100 kPa to about 3550 kPa.

11. A process for producing phenol from benzene, the process comprising:

(a) contacting benzene and hydrogen with a hydroalkylation catalyst under hydroalkylation conditions to produce cyclohexylbenzene;

(b) oxidizing at least a portion of the cyclohexylbenzene from (a) to produce an oxidation effluent stream comprising cyclohexylbenzene hydroperoxide and cyclohexylbenzene;

(c) cleaving the cyclohexylbenzene hydroperoxide in at least a portion of said oxidation effluent stream to produce a cleavage effluent stream comprising phenol, cyclohexanone, and cyclohexylbenzene, wherein the weight ratio of phenol to cyclohexanone in the cleavage effluent stream is about 0.7:1 to about 1.5:1;

(d) fractionating at least a portion of the cleavage effluent stream to produce (i) a first fraction richer in cyclohexanone than said portion of the cleavage effluent stream, said first fraction comprising no more than 50 wppm phenol, 0.1 wppm to 400 wppm of cyclohexanol, and 0.1 wppm to 100 wppm of at least one of methylcyclopentanone, cyclohexenol, cyclohexanedione, and hydroxycyclohexanone, said wppm amounts based on the total weight of the first fraction; and (ii) a second fraction richer in phenol and depleted in cyclohexanone as compared with said portion of the cleavage effluent stream, such that the weight ratio of phenol to cyclohexanone in said second fraction is about 2.0:1 to about 2.5:1;

(d-1) recovering the first fraction as a cyclohexanone product; and (e) contacting at least a portion of the second fraction with a dehydrogenation catalyst in a dehydrogenation reaction zone under dehydrogenation conditions effective to convert at least a portion of the cyclohexanone in said portion of the second fraction into phenol and cyclohexanol.

12. The process of claim 11, wherein the contacting (e) produces (i) a product stream comprising phenol, cyclohexanol, and cyclohexanone; and (ii) a hydrogen stream.

13. The process of claim 11, and further comprising:

(f) removing a third fraction comprising cyclohexylbenzene from at least a portion of the cleavage effluent stream so that said second fraction contains less than 2 wt % cyclohexylbenzene, based upon the total weight of the second fraction.

14. The process of claim 12, and further comprising:

(g) recovering a phenol-containing stream from said product stream to leave a residual stream depleted in phenol relative to the product stream and comprising cyclohexanol and cyclohexanone; and (h) contacting at least a portion of the residual stream with a dehydrogenation catalyst in a dehydrogenation reaction zone under dehydrogenation conditions effective to convert at least a portion of the cyclohexanone and cyclohexanol in said portion of the residual stream into phenol and produce a further product stream comprising phenol, cyclohexanone, and cyclohexanol, and a further hydrogen stream.

* * * * *